US011639910B2

(12) United States Patent
Ho et al.

(10) Patent No.: US 11,639,910 B2
(45) Date of Patent: May 2, 2023

(54) METHOD FOR FABRICATING ZINC OXIDE NANOSTRUCTURES AND GAS SENSORS

(71) Applicant: City University of Hong Kong, Hong Kong (CN)

(72) Inventors: Derek Ho, Hong Kong (CN); Ying Wang, Hong Kong (CN)

(73) Assignee: City University of Hong Kong, Hong Kong (CN)

( * ) Notice: Subject to any disclaimer, the term of this patent is extended or adjusted under 35 U.S.C. 154(b) by 52 days.

(21) Appl. No.: 17/449,288

(22) Filed: Sep. 29, 2021

(65) Prior Publication Data
US 2022/0113270 A1    Apr. 14, 2022

Related U.S. Application Data

(60) Provisional application No. 63/089,185, filed on Oct. 8, 2020.

(51) Int. Cl.
*G01N 27/12*    (2006.01)
*G01N 33/00*    (2006.01)

(52) U.S. Cl.
CPC ......... *G01N 27/127* (2013.01); *G01N 27/123* (2013.01); *G01N 33/0054* (2013.01)

(58) Field of Classification Search
CPC ............... G01N 27/127; G01N 27/123; G01N 33/0054; Y02A 50/20
See application file for complete search history.

(56) References Cited

FOREIGN PATENT DOCUMENTS

| CN | 103713019 A | * | 4/2014 | |
| CN | 106186045 A | * | 12/2016 | ............... C01G 9/02 |
| CN | 110935448 B | * | 11/2022 | ............... B01J 23/66 |

OTHER PUBLICATIONS

Chen et al. "Characteristics of ZnO nanorods-based ammonia gas sensors with a cross-linked configuration", Sensors and Actuators B 221 (2015) 491-498 (Year: 2015).*
Zhang et al. "Twinned tabour-like ZnO: Surfactant-, template-free synthesis and gas sensing behaviors", Applied Surface Science 257 (2011) 5784-5788 (Year: 2011).*
Hosseini et al. Room temperature H2S gas sensor based on rather aligned ZnO nanorods with flower-like structures, Sensors and Actuators B 207 (2015) 865-871 (Year: 2015).*
Fan et al. "The Fabrication of ZnO Microrods on Monolayer Graphene and Their Photocatalytic Application", Acta Chim. Slov. 2015, 62, 902-909. (Year: 2015).*
Zhang et al.; Metal-Organic Frameworks-Derived Hierarchical Co3O4 Structures as Efficient Sensing Materials for Acetone Detection. ACS Appl. Mater. Interfaces 2018, 10, 9765-9773.

(Continued)

*Primary Examiner* — Alvaro E Fortich
*Assistant Examiner* — Dilara Sultana
(74) *Attorney, Agent, or Firm* — S&F/WEHRW

(57) ABSTRACT

The present disclosure provides a gas sensor comprising a gas sensing layer fabricated based on a solution-processed, template-free synthesis method that achieves controllable ZnO nanostructured morphologies. The method is based on promotion and suppression of growth at specific crystallographic dimensions by tuning the polarity of the solvent. The gas sensing layer with the ZnO nanostructures exhibits high response, excellent selectivity and rapid recovery time.

18 Claims, 7 Drawing Sheets

(56) References Cited

OTHER PUBLICATIONS

Qu et al.; Low Working-Temperature Acetone Vapor Sensor Based on Zinc Nitride and Oxide Hybrid Composites. Small, 2016, 12, 3128-3133.

Kwak et al.; Molybdenum Trioxide (α-MoO3) Nanoribbons for Ultrasensitive Ammonia (NH3) Gas Detection: Integrated Experimental and Density Functional Theory Simulation Studies ACS Appl. Mater. Interfaces 2019, 11, 10697-10706.

Liu et al.; Acidic Site-Assisted Ammonia Sensing of Novel CuSbS2 Quantum Dots/Reduced Graphene Oxide Composites with an Ultralow Detection Limit at Room Temperature. ACS Appl. Mater. Interfaces 2019, 11, 9573-9582.

Raza et al.; Gas Sensing of NiO-SCCNT Core-Shell Heterostructures: Optimization by Radial Modulation of the Hole Accumulation Layer. Adv. Funct. Mater. 2020, 30, 1906874.

Zhao et al.; Design of Au@WO3 core-shell structured nanospheres for ppb-level NO2 sensing. Sens. Actuators, B 2019, 282, 917-926.

Zhang et al.; Rapid sensitive sensing platform based on yolk-shell hybrid hollow sphere for detection of ethanol. Sens. Actuators, B 2018, 256, 479-487.

Zhou et al.; Effect of Cation Substitution on the Gas-Sensing Performances of Ternary Spinel MCo2O4 (M=Mn, Ni, and Zn) Multishelled Hollow Twin Spheres. ACS Appl. Mater. Interfaces 2019,11, 28023-28032.

Wei et al.; Hollow Structural Transition Metal Oxide for Advanced Supercapacitors. Adv. Mater. Interfaces 2018, 5, 1701509.

Yang et al.; One step synthesis of branched SnO2/ZnO heterostructures and their enhanced gas-sensing properties. Sens. Actuators, B 2019, 281, 415-423.

Chao et al.; Facile fabrication of ZnO/C nanoporous fibers and ZnO hollow spheres for high performance gas sensor. Sens. Actuators, B 2019, 298, 126927.

Li et al.; Soft-templated formation of double-shelled ZnO hollow microspheres for acetone gas sensing at low concentration/near room temperature. Sens. Actuators, B 2018, 273, 751-759.

Zhang et al.; Hierarchical Nanoheterostructure of Tungsten Disulfide Nanoflowers Doped with Zinc Oxide Hollow Spheres: Benzene Gas Sensing Properties and First-Principles Study. ACS Appl. Mater. Interfaces 2019, 11, 31245-31256.

Zhang et al.; Novel SnO2@ZnO hierarchical nanostructures for highly sensitive and selective NO2 gas sensing. Sens. Actuators, B 2018, 257, 714-727.

Zhou et al.; Highly Enhanced Sensing Properties for ZnO Nanoparticle-Decorated Round-Edged α-Fe2O3 Hexahedrons. ACS Appl. Mater. Interfaces 2015, 7, 8743-8749.

Wang et al.; Realizing the Control of Electronic Energy Level Structure and Gas Sensing Selectivity over Heteroatom-Doped In2O3 Spheres with an Inverse Opal Microstructure. ACS Appl. Mater. Interfaces 2019, 11, 9600-9611.

Pal et al.; Faceted metal and metal oxide nanoparticles: design, fabrication and catalysis. Nanoscale, 2015, 7, 14159-14190.

Zhang et al.; Control of ZnO Morphology via a Simple Solution Route. Chem. Mater. 2002, 14, 4172-4177.

Xu et al.; One-Dimensional ZnO Nanostructures: Solution Growth and Functional Properties. Nano Res. 2011, 4(11),1013-1098.

Yu et al.; A Versatile Method to Enhance the Operational Current of Air Stable Organic Gas Sensor for Monitoring of Breath Ammonia in Hemodialysis Patients. ACS Sens. 2019, 4, 1023-1031.

Meng et al.; Pt/WN based fuel cell type methanol sensor. Sens. Actuators, B 2020, 307, 127686.

Liu et al.; A highly sensitive and moisture-resistant gas sensor for diabetes diagnosis with Pt@In2O3 nanowires and a molecular sieve for protection. NPG Asia Materials, 2018, 10, 293-308.

Poloju et al.; Enhancement of the isopropanol gas sensing performance of SnO2/ZnO core/shell nanocomposites. J. Mater. Chem. C 2017, 5, 2662.

Patil et al.; Cr2O3—activated ZnO thick film resistors for ammonia gas sensing operable at room temperature. Sens. Actuators, B 2007, 126, 368-374.

Bahu et al.; CuO—ZnO semiconductor gas sensor for ammonia at room temperature. J. Electron. Devices, 2012, 14, 1137-1141.

Ravichandran et al.; Effect of tungsten doping on the ammonia vapor sensing ability of ZnO thin films prepared by a cost-effective simplified spray technique. Surfaces and Interfaces, 2020, 18, 100412.

Mani et al.; Selective detection of ammonia using spray pyrolysis deposited pure and nickel doped ZnO thin films. Appl. Surf. Sci. 2014, 311, 405-412.

Tai et al.; ZnO nanoparticles/ reduced graphene oxide bilayer thin films for improved NH3-sensing performances at room temperature. Nanoscale Res. Lett.2016, 11, 2-8.

Li et al.; NH3 sensing properties of ZnO thin films prepared via sol-gel method. J. Alloys Compd. 2014, 606, 27-31.

Yamazoe; New approaches for improving semiconductor gas sensors. Sens. Actuators, B 1991, 5, 7-19.

Barsen et al.; Conduction Model of Metal Oxide Gas Sensors. Journal of Electroceramics, 2001, 7, 143-167.

Qu et al.; Programmed Synthesis of Sn3N4 Nanoparticles via a Soft Chemistry Approach with Urea: Application for Ethanol Vapor Sensing. Chem. Mater. 2017, 29, 969-974.

Wang et al.; Ultraselective acetone-gas sensor based ZnO flowers functionalized by Au nanoparticle loading on certain facet. Sens. Actuators, B 2019, 288, 1-11.

Shimizu et al.; Basic aspects and challenges of semiconductor gas sensors. MRS Bull. 1999, 24, 18-24.

Cui et al.; UV-light illumination room temperature HCHO gas-sensing mechanism of ZnO with different nanostructures. Sens. Actuators, B 2016, 227, 220-226.

Rothschild et al.; The effect of grain size on the sensitivity of nanocrystalline metal-oxide gas sensors. J. Appl. Phys 2004, 95, 6374.

\* cited by examiner

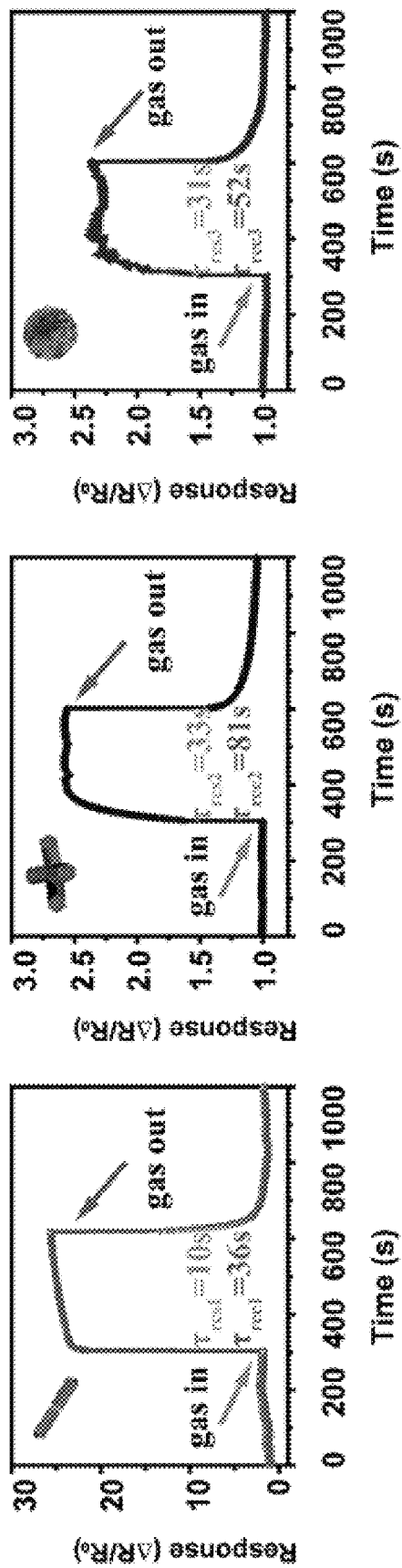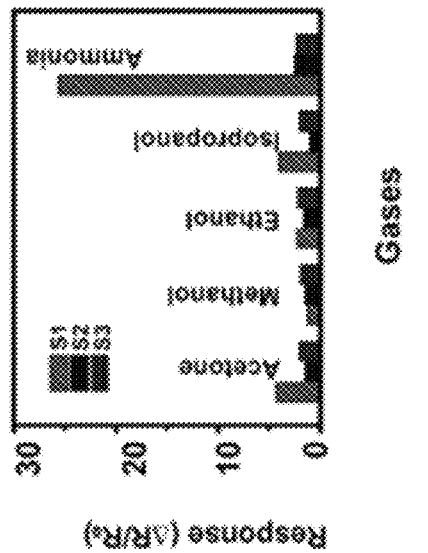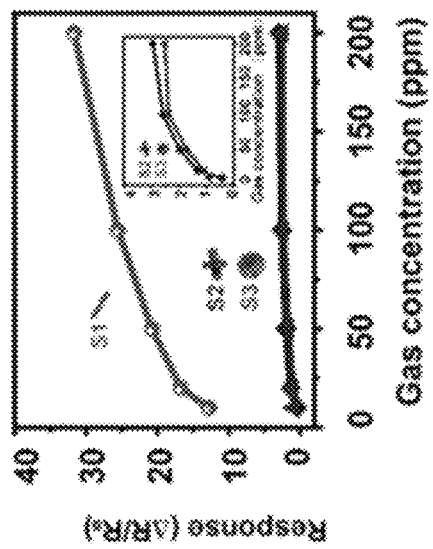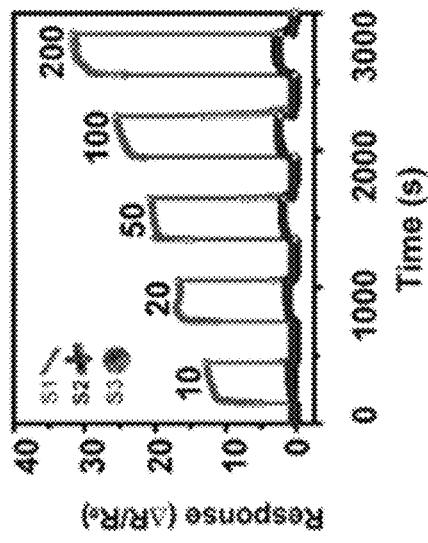
Figure 7A  Figure 7B  Figure 7C
Figure 7D  Figure 7E  Figure 7F

METHOD FOR FABRICATING ZINC OXIDE NANOSTRUCTURES AND GAS SENSORS

CROSS-REFERENCE TO RELATED APPLICATIONS

This application claims the benefit of U.S. Provisional Patent Application No. 63/089,185, filed on Oct. 8, 2020, which is incorporated by reference herein in its entirety.

TECHNICAL FIELD

The present disclosure relates a method for fabricating zinc oxide nanostructures and their application to gas sensors.

BACKGROUND

A high level of control of the environment can be achieved by the ubiquitous deployment of advanced environmental sensors, for example, in detection of toxic airborne contaminants. Ammonia, one of the most widely used substance in fertilizers and industrial coolants, has been shown to cause serious harm to the environment and humans. Inhalation concentration should be limited to no more than 25 ppm over 8 h or 35 ppm over 10 min. Therefore, ammonia detection is of significance to prevent acute poisoning.

Advanced environmental sensors that are suitable for ubiquitous and inexpensive deployment for the detection of toxic airborne contaminants are of urgent demand. Thin films of transition metal oxides (TMO) (i.e., a gas sensing layer) such as NiO, $WO_3$ represent the most prominent class of material for commercial gas sensors, due to their high sensitivity, ease of fabrication and chemical stability. The work principle of metal oxide semiconductor gas sensors is resistance modulation upon the adsorption of the target gas and oxygen species.

Morphological control of nanostructures has become an indispensable approach to achieve a performance level beyond those achievable by conventional bulk materials and thin films. Recently, nanostructures of TMO offer access to the enhancement of surface area and tuning of electronic transport characteristics. Hard-templating methods, soft-templating methods and template free methods have been studied extensively to construct ordered TMO structures. However, template based methods suffered from complex, multi-step procedures, whereas, template free methods can significantly simplify the synthetic process. Branched ZnO crystals have been prepared by using an aqueous solution-synthesis approach to grow oriented nanostructures by taking advantage of the preferential adsorption of different facets of hexagonal ZnO. Hollow ZnO spheres have been prepared by the Ostwald ripening process.

Double shelled ZnO hollow microspheres have been synthesized from exploring the competition between the contraction force due to dissolution and the adhesion force due to crystallization. Zinc Oxide hollow spheres have been prepared by using a self-assembly approach. Although significant advances have been made in solution-based and template-free synthesis of TMO nanostructures, existing methods remain rather tedious and unreliable. For examples, the conventional gas sensors based on nanostructured oxide materials still suffer from complex, multi-step fabrication processes and lack of uniformity in the synthesized products.

A need therefore exists for improved ZnO nanostructures for gas sensors and an improved method for fabricating the same that eliminate or at least diminish the disadvantages and problems described above.

SUMMARY

Provided herein is a method for fabricating a zinc oxide (ZnO) structure comprising: providing a polar solvent with a predetermined polarity; mixing at least a zinc salt and the polar solvent thereby forming a mixture; heating the mixture under a pressure thereby forming a precipitate; separating the precipitate from the heated mixture; and drying the separated precipitate to form the ZnO structure.

In certain embodiments, the method further comprises calcinating the dried precipitate.

In certain embodiments, the ZnO structure is a twin-rod-shaped ZnO structure, a cross-shaped ZnO structure, or a flower-shaped ZnO structure.

In certain embodiments, the polar solvent consists of water for forming the twin-rod-shaped ZnO structure; and the polar solvent consists of ethanol for forming the flower-shaped ZnO structure.

In certain embodiments, the polar solvent consists of water and ethanol for forming the cross-shaped ZnO structure.

In certain embodiments, a volume ratio of the water to the ethanol is of 0.8:1 to 1.2:1.

In certain embodiments, the step of providing a polar solvent comprise mixing a plurality of first polar solvents in a volume ratio to form the polar solvent with the predetermined polarity, wherein the plurality of first polar solvents has different polarities.

In certain embodiments, the step of providing a polar solvent comprises mixing a first polar solvent and a second polar solvent in a volume ratio to form the polar solvent with the predetermined polarity, wherein the first polar solvent and the second polar solvent have different polarities.

In certain embodiments, the zinc salt is zinc nitrate; and the step of mixing at least a zinc salt and the polar solvent comprises mixing the zinc nitrate, the polar solvent, hexamethylenetetramine, polyvinylpyrrolidone and polyvinyl alcohol thereby forming the mixture.

Provided herein is a gas sensor comprising: a gas sensing layer for sensing variation in a concentration of a gas and generating a change in electrical resistance, the gas sensing layer comprising a ZnO structure, the ZnO structure being a twin-rod-shaped ZnO structure, a cross-shaped ZnO structure or a flower-shaped ZnO structure.

In certain embodiments, the gas sensor further comprises a ceramic tube; two electrodes separately attached to an outer surface of the ceramic tube; two electrode lines attached to the two electrode respectively; and a heating element located inside the ceramic tube; wherein the gas sensing layer electrically connects the two electrodes.

In certain embodiments, the ceramic tube comprises aluminum oxide; each of the two electrodes is a gold electrode; each of the two electrode line is a platinum wire; the heater is a nickel-chromium coil; and the gas sensing layer at least partially covers the outer surface of the ceramic tube.

Provided herein is an ammonia gas sensor comprising: a gas sensing layer for sensing variation in a concentration of ammonia gas and generating a change in electrical resistance, the gas sensing layer comprising zinc oxide (ZnO) twinned rods.

In certain embodiments, the ZnO twinned rods comprise two ZnO rods, which are connected in series.

In certain embodiments, the ZnO twinned rods have an elongated-hexagonal shape.

In certain embodiments, the ZnO twinned rods have an aspect ratio of diameter to height being of 1:4 to 1:10, and an average grain size of 32 to 34 nm.

In certain embodiments, the ZnO twinned rods have a diameter of 500 nm to 3 μm, and a height of 5 μm to 10 μm.

In certain embodiments, the gas sensing layer has a thickness of 200 μm to 400 μm.

In certain embodiments, the ammonia gas sensor further comprises: a ceramic tube; two electrodes separately attached to an outer surface of the ceramic tube; two electrode lines attached to the two electrode respectively; and a heating element located inside the ceramic tube; wherein the gas sensing layer electrically connects the two electrodes.

In certain embodiments, the ceramic tube comprises aluminum oxide; each of the two electrodes is a gold electrode; each of the two electrode line is a platinum wire; the heater is a nickel-chromium coil; and the gas sensing layer at least partially covers the outer surface of the ceramic tube.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Other aspects of the present invention are disclosed as illustrated by the embodiments hereinafter.

BRIEF DESCRIPTION OF DRAWINGS

The appended drawings, where like reference numerals refer to identical or functionally similar elements, contain figures of certain embodiments to further illustrate and clarify the above and other aspects, advantages and features of the present invention. It will be appreciated that these drawings depict embodiments of the invention and are not intended to limit its scope. The invention will be described and explained with additional specificity and detail through the use of the accompanying drawings in which:

FIG. 7A shows a dynamic responses towards 100 ppm ammonia for an ammonia gas sensor fabricated based on ZnO twin-nanorods;

FIG. 7B shows a dynamic responses towards 100 ppm ammonia for an ammonia gas sensor fabricated based on ZnO nanocrosses;

FIG. 7C shows a dynamic responses towards 100 ppm ammonia for an ammonia gas sensor fabricated based on ZnO nanoflowers;

FIG. 7D shows dynamic responses of ZnO twinned nanorods, ZnO nanocross and ZnO nanoflower across different concentrations (10-200 ppm) of ammonia;

FIG. 7E shows static response curves of ZnO twinned nanorods, ZnO nanocross and ZnO nanoflower across different concentrations (10-200 ppm) of ammonia;

FIG. 7F shows responses to 100 ppm of various gases for ZnO twinned nanorods, ZnO nanocross and ZnO nanoflower;

Figure 1:
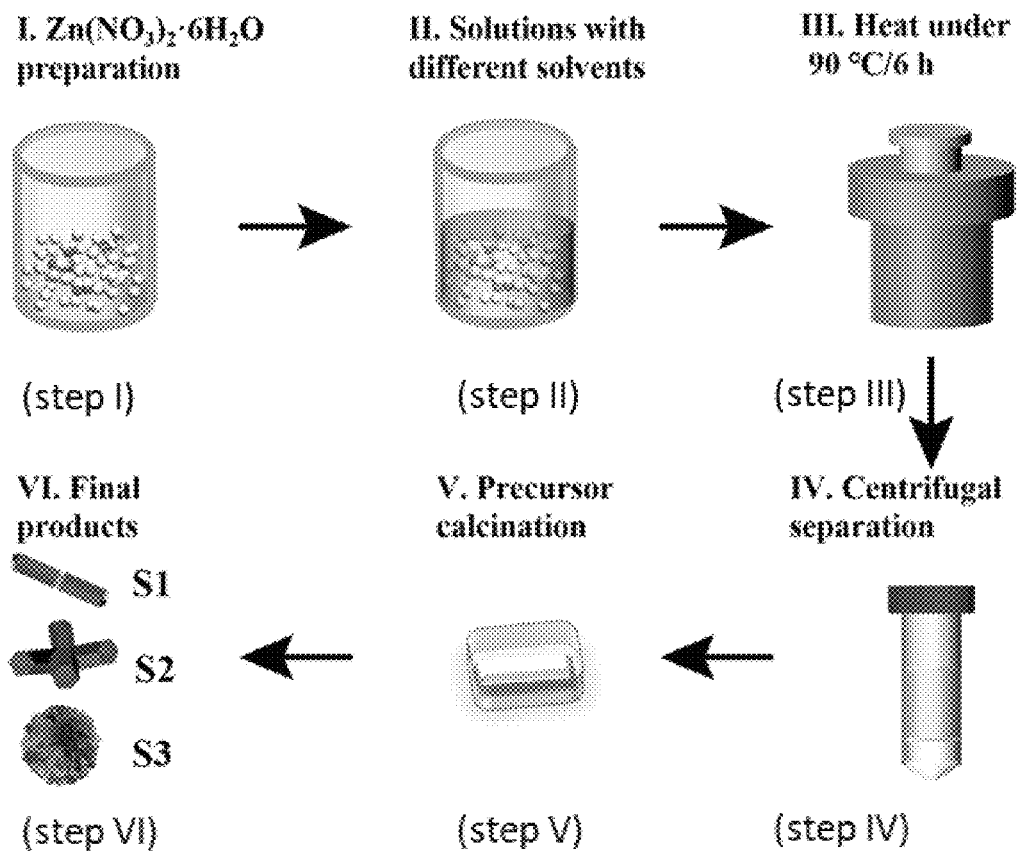
FIG. 1 is a schematic depicting steps for fabricating different ZnO nanostructures of gas sensing layer according to certain embodiments.

Skilled artisans will appreciate that elements in the figures are illustrated for simplicity and clarity and have not necessarily been depicted to scale.

DETAILED DESCRIPTION OF THE INVENTION

It will be apparent to those skilled in the art that modifications, including additions and/or substitutions, may be made without departing from the scope and spirit of the invention. Specific details may be omitted so as not to obscure the invention; however, the disclosure is written to enable one skilled in the art to practice the teachings herein without undue experimentation.

An aspect of the present disclosure provides a gas sensor comprising a gas sensing layer fabricated based on a solution-processed, template-free synthesis method that achieves controllable ZnO nanostructured/structured morphologies. The method is based on promotion and suppression of growth at specific crystallographic dimensions by tuning the polarity of the solvent.

Certain embodiments provide gas sensor comprising: a gas sensing layer for sensing variation in a concentration of a gas and generating a change in electrical resistance, the gas sensing layer comprising a ZnO nanostructure, the ZnO nanostructure being a twin-rod-shaped ZnO nanostructure, a cross-shaped ZnO nanostructure or a flower-shaped ZnO nanostructure.

In certain embodiments, the gas sensor further comprises: a ceramic tube; two electrodes separately attached to an outer surface of the ceramic tube; two electrode lines attached to the two electrode respectively; and a heating element located inside the ceramic tube; wherein the gas sensing layer electrically connects the two electrodes.

In certain embodiments, the ceramic tube comprises aluminum oxide; each of the two electrodes is a gold electrode; each of the two electrode line is a platinum wire; the heater is a nickel-chromium coil; and the gas sensing layer at least partially covers the outer surface of the ceramic tube.

Certain embodiments provide a method for fabricating a zinc oxide nanostructure (or structure) comprising: manipulating polarity of a polar solvent; mixing at least a zinc salt and the polar solvent thereby forming a mixture; heating the mixture beyond 150 degrees C. and under a pressure beyond atmospheric pressure thereby forming a precipitate; separating the precipitate from the heated mixture; and drying the separated precipitate to form the ZnO nanostructure.

In certain embodiments, the method further comprises calcinating the dried precipitate for the purpose of achieving greater crystallinity, thus better sensing performance.

In certain embodiments, the ZnO nanostructure is a twin-rod-shaped ZnO nanostructure, a cross-shaped ZnO nanostructure, or a flower-shaped ZnO nanostructure.

In certain embodiments, the polar solvent consists of water for forming the twin-rod-shaped ZnO nanostructure; and the polar solvent consists of ethanol for forming the flower-shaped ZnO nanostructure.

In certain embodiments, the polar solvent consists of water and ethanol for forming the cross-shaped ZnO nanostructure.

In certain embodiments, a volume ratio of the water to the ethanol is of 0.8:1 to 1.2:1.

In certain embodiments, the step of manipulating polarity of a polar solvent comprise mixing a plurality of first polar solvents in a volume ratio to form the polar solvent, wherein the plurality of first polar solvents has different polarities.

In certain embodiments, the step of manipulating polarity of a polar solvent comprises mixing a first polar solvent and a second polar solvent in a volume ratio to form the polar solvent, wherein the first polar solvent and the second polar solvent have different polarities.

In certain embodiments, wherein the zinc salt is zinc nitrate; and the step of mixing at least a zinc salt and the polar solvent comprises mixing the zinc nitrate, the polar solvent, hexamethylenetetramine, polyvinylpyrrolidone and polyvinyl alcohol thereby forming the mixture.

Another aspect of the present disclosure provides an ammonia gas sensor comprising a gas sensing layer fabricated based on a solution-processed, template-free synthesis method that achieves controllable ZnO nanostructured/structured morphologies. The method is based on promotion and suppression of growth at specific crystallographic dimensions by tuning the polarity of the solvent. Ammonia gas sensors based on three nanostructured morphologies have been fabricated and characterized. Specifically, ZnO twinned rods exhibited the high response and excellent selectivity to ammonia vapor at the operating temperature of 280° C. with a rapid response and recovery times of 10 s and 36 s, respectively. Investigation of the structure-performances relationship reveals that controlled enhancement and suppression to growth along crystallographic dimensions is an effective strategy for achieving desirable gas sensing properties. In certain embodiments, enhanced c-axis growth while suppressing growth in other crystallographic dimensions is an effective way for tuning the gas sensing properties.

Certain embodiments provide an ammonia gas sensor comprising: a gas sensing layer for sensing variation in a concentration of ammonia gas and generating a change in electrical resistance, the gas sensing layer comprising zinc oxide (ZnO) twinned rods.

In certain embodiments, the ZnO twinned rods comprise two crystalline ZnO rods, which are connected in series.

In certain embodiments, the ZnO twinned rods have an elongated-hexagonal shape.

In certain embodiments, the ZnO twinned rods have an aspect ratio of diameter to height being of 1:4 to 1:10, and an average grain size of 32 to 34 nm.

In certain embodiments, the ZnO twinned rods have a diameter of 500 nm to 3 µm, and a height of 5 µm to 10 µm.

In certain embodiments, the gas sensing layer has a thickness of 200 µm to 400 µm.

In certain embodiments, the ammonia gas sensor further comprises: a ceramic tube; two electrodes separately attached to an outer surface of the tube; two electrode lines attached to the two electrode respectively; and a heating element located inside the tube; wherein the gas sensing layer electrically connects the two electrodes.

In certain embodiments, the ceramic tube comprises aluminum oxide; each of the two electrodes is a gold electrode; each of the two electrode line is a platinum wire; the heater is a nickel-chromium coil; and the gas sensing layer at least partially covers the outer surface of the tube.

FIG. 1 is a schematic depicting steps for fabricating different ZnO nanostructures according to certain embodiments. In step I, zinc nitrate hexahydrate ($Zn(NO_3)_2.6H_2O$) as a zinc salt is provided. In step II, zinc nitrate hexahydrate is mixed with three polar solvents having different polarities to form three mixtures respectively. In step III, each of the mixtures is heated at 90° C. for 6 hr in an autoclave to form a precipitate. In step IV, the precipitate is collected from the mixture by centrifugation separation and dried. In step V, each the precipitates is calcinated. In step VI, three types of ZnO nanostructures, including twinned ZnO nanorods, a ZnO nanocross and a ZnO nanoflower, are obtained.

Figure 2A:
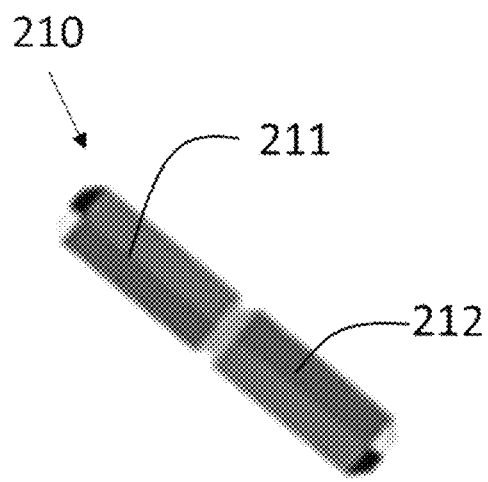
FIG. 2A is a schematic diagram depicting ZnO twinned nanorods according to certain embodiments.

FIG. 2A is a schematic diagram depicting ZnO twinned nanorods 210 according to certain embodiments. The ZnO twinned nanorods 210 have an elongated-hexagonal shape and comprise two hexagonal crystalline ZnO nanorods 211, 212, which are connected in series.

Figure 2B:
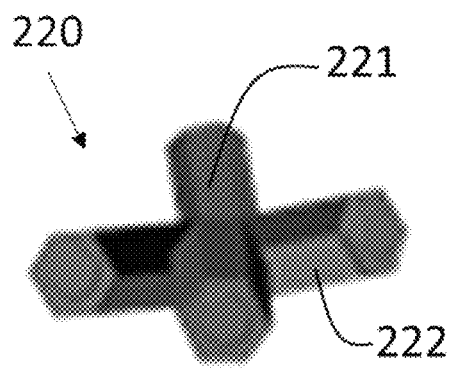
FIG. 2B is a schematic diagram depicting a ZnO nanocross according to certain embodiments.

FIG. 2B is a schematic diagram depicting a ZnO nanocross 220 according to certain embodiments. The ZnO nanocross 220 comprises two hexagonal crystalline ZnO nanorods 221, 222 which are intersected to provide a cross shape.

Figure 2C:
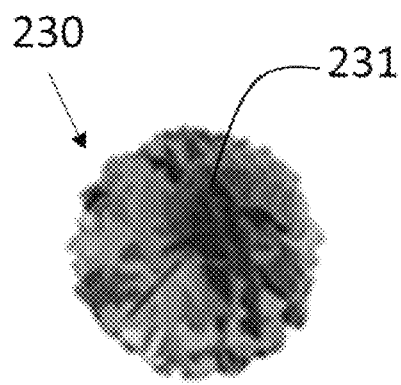
FIG. 2C is a schematic diagram depicting a ZnO nanoflower according to certain embodiments.

FIG. 2C is a schematic diagram depicting a ZnO nanoflower 230 according to certain embodiments. The ZnO nanoflower 230 comprises a plurality of nanosheets 231, which are assembled to resemble a flower.

Figure 3:
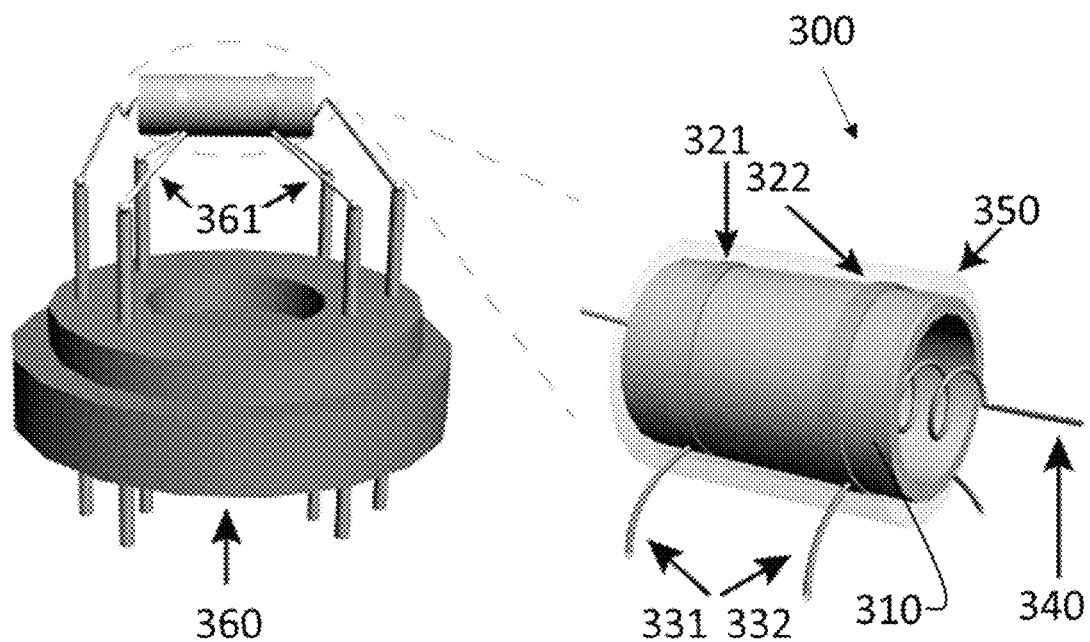
FIG. 3 is a schematic depicting a gas sensor structure according to certain embodiments.

FIG. 3 is a schematic depicting a gas sensor structure 300 according to certain embodiments. The gas sensor structure 300 comprises a ceramic tube 310, two electrodes 321, 322 (e.g., Au electrodes), two electrode lines 331, 332 (e.g., Pt wires), a heating element 340 (e.g., Ni—Cr alloy coils) and a gas sensing layer 350. The two electrodes 321, 322 are separately attached to an outer surface of the ceramic tube 310. The two electrode lines 331, 332 are attached to the two electrode 321, 322 respectively. The heating element 340 is located inside the ceramic tube 310. The gas sensing layer 350 covers the outer surface of the ceramic tube 310 and the two electrodes 321, 322, and electrically connects the two electrodes 321, 322. The gas sensor structure 300 is mounted on a socket 360 having pins 361 for connecting to the electrodes 321, 322 and the electrode lines 331, 332.

EXAMPLES

Materials

Zinc nitrate hexahydrate ($Zn(NO_3)_2.6H_2O$), polyvinylpyrrolidone (PVP, $M_W$=1.3 Mg mol$^{-1}$), polyvinyl alcohol (PVA1788, $(CH_2CHOH)_n$) were purchased from Aldrich. Hexamethylenetetramine HMTA ($(CH_2)_6N_4$) was purchased from BDH Chemicals. All materials were used without further purification.

Synthesis

The preparation of different ZnO nanostructures is depicted in FIG. 1 and described as follows: 0.297 g Zn(NO$_3$)$_2$·6H$_2$O, 0.35 g HMTA, 0.4 g PVP and 0.1 g PVA were dissolved in three different solvents: (i) 20 ml deionized water, (ii) 10 ml deionized water and 10 ml ethanol, and (iii) 20 ml ethanol, where the synthesized products are denoted samples S1, S2, and S3, respectively. After the primary salt was dissolved completely, the resulting white suspension was transferred into a 50 mL Teflon-lined stainless autoclave, which was kept at 90° C. for 6 h in an oven. Subsequently, the autoclave was cooled down to room temperature naturally. The precipitate was collected by centrifugation and alternately washed several times with ethanol and deionized water, then dried in air at 60° C. for 24 h. Finally, calcination of the dried precipitate at 450° C. (initially from room temperature, ramped up at 2° C./min) in a tube furnace for 3 h in air resulted in products with different morphologies.

Characterization

X-Ray diffraction (XRD) analysis was conducted by a Bruker D2 Phaser X-ray diffractometer with Cu K$_\alpha$ radiation ($\lambda$=1.54 Å) to analyze the structure of the prepared products. Morphological characterization was performed by field emission scanning electron microscopy (FE-SEM) (JEOL JSM-6335F) with a scan voltage of 5 kV.

Fabrication of Gas Sensor

The sensor device structure is shown in FIG. 3. To form a homogenous solution for a gas sensing layer, 0.1 mg of the as-prepared material was evenly mixed with 25 µL of deionized water. To form a gas sensing layer with a thickness of 300 µm, the solution was then dropped onto a hollow Al$_2$O$_3$ ceramic tube (4 mm in length, external diameter of 1.2 mm, and internal diameter of 0.8 mm) with two parallel Au electrodes pre-printed on the tube. After the tube was dried at 80° C. for 24 h, a Ni—Cr alloy coil was used as a heater for controlling the operating temperature. The gas sensor was then heat treated at 200° C. for 2 h and aged at the 80° C. for 170 h.

Gas Sensing Characterization System

Gas sensing properties were characterized using a custom-built system consisting a computer, data collection system (CGS-8 intelligent gas sensing analysis system and corresponding test software), and custom test chambers (1 L). The characterization system supports the testing of all three samples by simultaneously subjecting them to the same environment, which is critical for an accurate comparison between the devices. Characterization proceeded as follows: in the beginning, sensors were placed into a chamber filled with air until the resistances of all sensors were stable. To prepare the ammonia target gas, a controlled amount of ammonia solution was injected into an evaporator to form ammonia vapor. After the sensor responses reached steady state, the test chamber was flushed with air to allow sensor recovery. To minimize variation across measurements, the entire process of target introduction and recording was fully automated by a computer system.

The gas response $$(S) \text{ is defined as} = \frac{|R_g - R_0|}{R_0} = \frac{\Delta R}{R_0},$$

where $R_0$, $R_g$, and $\Delta R$ denote the initial resistance of the sensor placed in air, measured resistance exposed to the target gas, and absolute value of resistance changes, respectively. As conventional, $\tau_{res}$ and $\tau_{rec}$ are defined as the time taken by the sensor to achieve 90% of the final resistance value for both the response and recovery times. Specifically, the response time reflects the resistance change from $R_0$ to $R_0-\Delta R \times 90\%$ upon the introduction of the target gas to the sensor. The recovery time is defined as the time taken for the resistance to change from $R_g$ to $R_g+\Delta R \times 90\%$ upon the flushing of the test chamber with air.

Morphological Characteristics

Figures 4A, 4B:
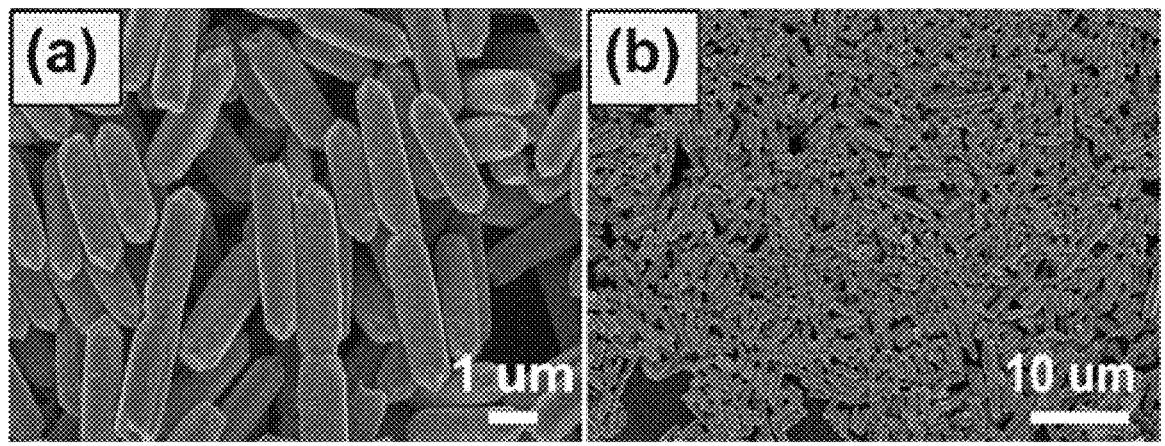
FIG. 4A shows the morphology of the as-synthesized ZnO twinned nanorods in high magnification.
FIG. 4B shows the morphology of the as-synthesized ZnO twinned nanorods in low magnification.
Figure 4C:
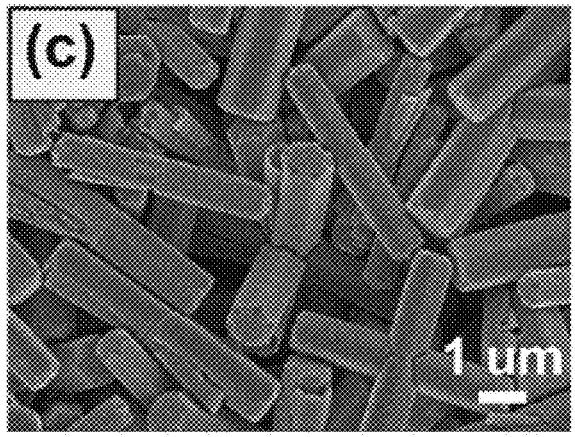
FIG. 4C shows the morphology of the as-synthesized ZnO nanocross in high magnification.
Figure 4D:
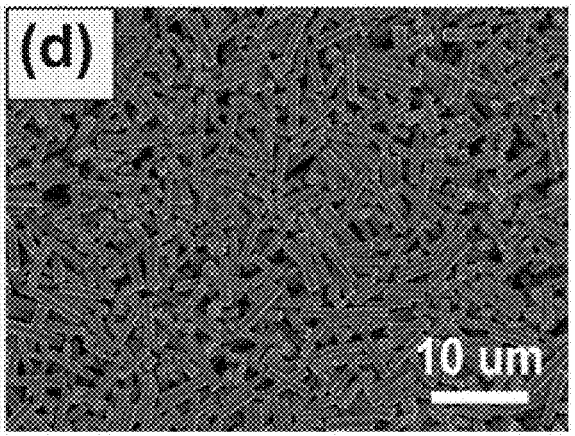
FIG. 4D shows the morphology of the as-synthesized ZnO nanocross in low magnification.
Figure 4E:
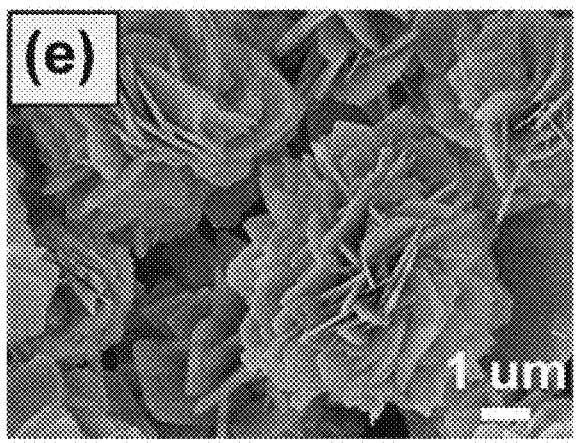
FIG. 4E shows the morphology of the as-synthesized ZnO nanoflower in high magnification.
Figure 4F:
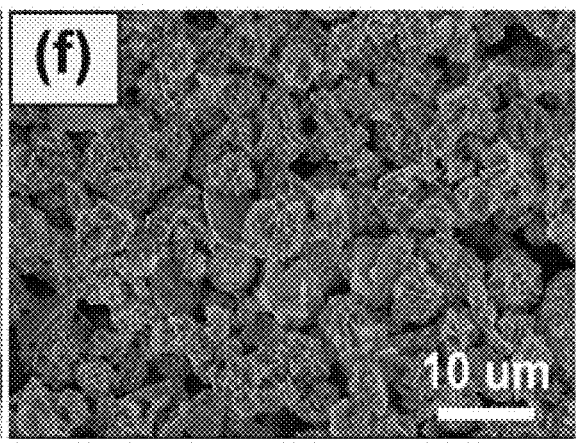
FIG. 4F shows the morphology of the as-synthesized ZnO nanoflower in low magnification.

The morphologies of the as-synthesized ZnO nanostructures were characterized by FE-SEM. FIG. 4A and FIG. 4B show the magnified and wide-field images of sample S1, revealing its symmetric twin-nanorod structure, with an average cross-sectional length (herein, referred to as diameter) of 1 µm. FIG. 4C and FIG. 4D show the nanocross morphology of sample S2, with an average hexagonal rod diameter of 1.5 µm. FIG. 4E and FIG. 4F show the nanoflowers morphology of sample S3, showing an average diameter of 4.5 µm. The nanoflowers are assembled by many nanosheets with thicknesses of 20 nm and a rough surface. It is evident from the wide-field SEMs of FIGS. 4B, 4D and 4F that the morphology and size of the synthesized structures are highly uniform.

Structural Characteristics

Figure 5:
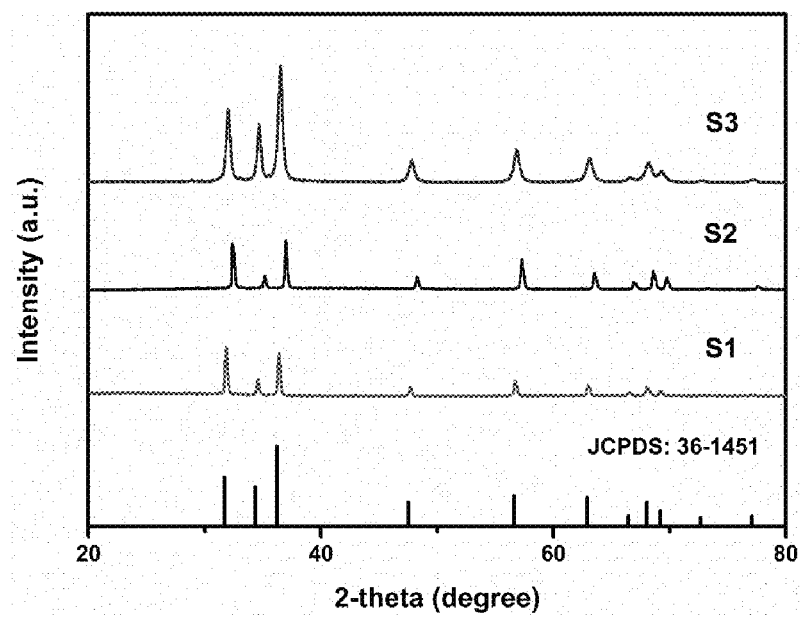
FIG. 5 shows XRD patterns of the as-synthesized ZnO twinned nanorods, ZnO nanocross and ZnO nanoflower respectively.

To characterize the crystal structures of ZnO, the XRD peaks of the as-synthesized samples are shown in FIG. 5. Evidently, the diffraction peaks can be attributed to the wurtzite structure (JCPDS, No. 36-1451). No other characteristic peaks appear throughout the pattern, which reflects that the product is of high purity. The detailed crystal information is described as following. Using Scherrer's equation, $$D = \frac{k\lambda}{\beta\cos\theta},$$

the average grain sizes of all samples can be obtained, where D is the grain size, κ is a constant related to the crystallite shape, typically taken as 0.9, $\lambda$ is the X-ray wavelength, $\beta$ is the peak width of the diffraction peak profile at half maximum height, and $\theta$ is the diffraction angle. The average grain size for S1, S2 and S3 can be estimated to be 32.9 nm, 47.0 nm and 47.4 nm, respectively.

Formation Mechanisms Discussion

Figure 6:
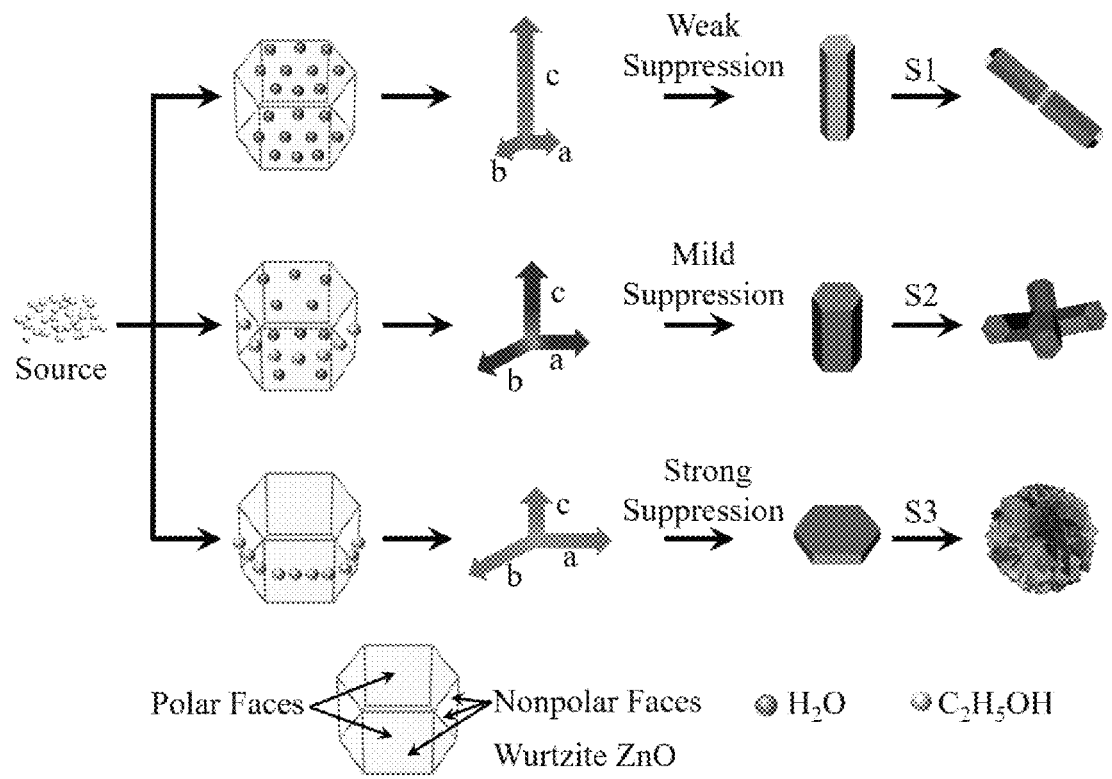
FIG. 6 shows a schematic of the formation mechanisms of ZnO crystals across different suppression of c-axis growth.

FIG. 6 illustrates the mechanism of morphological control via the use of different solvents. The formation of twin-rod, nanocross and nanoflower ZnO crystals can be attributed to the difference in the growth velocities of various crystal facets. Specifically, the polarity of the solvent can be rationally designed to interact specifically to the polar and nonpolar surfaces of the Wurtzite ZnO crystal structure. The polar solvent molecules have stronger interactions with the polar surfaces of ZnO to provide oxygen molecules, which react with Zn$^{2+}$ ions, to form the ZnO crystal. In contrast, the interaction between a polar solvent with nonpolar crystallographic faces is weak. As the solvent gradually changes from the more polar solvent (water), to the less polar solvent (ethanol), the solvent molecules interactions with the polar surfaces (0 0 1) are suppressed, but the interaction with the nonpolar surfaces are enhanced.

For the formation of the twin-rod ZnO crystal (sample S1), when water serves as the solvent, the solvent polarity is the largest among the samples. Thus, the largest amount of O$^{2-}$ ions are absorbed on the polar surfaces, (0 0 1), leading to the fastest crystal growth along the c-axis, while growth perpendicular to the c-axis is suppressed. For the nanocross morphology (sample S2), as the solvent is a mixture of water and ethanol, with reduced solvent polarity, less $O^{2-}$ ions are absorbed on the (0 0 1) polar surfaces and more $O^{2-}$ ions are absorbed on the nonpolar surfaces, leading to slower crystal growth along the c-axis and more growth perpendicular to the c-axis.

For the nanoflower morphology (sample S3), when the solvent contents only ethanol, solvent polarity is the weakest, thus the most $O^{2-}$ ions are absorbed on the nonpolar surfaces. This leads to the greatest suppression of c-axis growth, but simultaneously, growth in other crystallographic directions is augmented.

Gas Sensing Properties

Gas sensing properties are characterized for the three morphologically different samples. The response and recovery time, $\tau_{res}$ and $\tau_{rec}$, for all three sensors towards 100 ppm ammonia vapor are shown in FIG. 7A-7C. All tests were performed at 280° C. Evidently, the nanorods exhibit the fastest response and recovery time of 10 s and 36 s. S1 also exhibits the largest response. In contrast, the nanocross (S2) and nanoflower (S3) have smaller responses and slower dynamics.

FIG. 7D shows the dynamic performance of sensors based on S1-S3 for a range of ammonia vapor concentrations (10-200 ppm). It is evident that, as the concentration increases, the responses increase according to the classical exponential relationship. All sensors can rapidly respond to the target gas and fully return to the baseline subsequently, which is an important and highly desirable sensor characteristic.

FIG. 7E replots the data of FIG. 7D in terms of the response across various concentrations. All sensors exhibited a rapid increase in response when exposed to ammonia in the lower concentration range. However, the responses begin to saturate in the high ammonia concentration range, which is typical of gas sensors, as the sensing surface is saturated with the target gas molecules. Specifically, a large amount of target gas molecules creates a deficiency of surface-adsorbed oxygen species, which is an integrate part of the reaction responsible for generating a response.

A selective ammonia sensor should have the ability to recognize the ammonia molecule in the presence of other widely used volatile organic compounds (VOCs). In disease diagnostics applications, ammonia is often required to be sensed in the presence of a variety of bio-generated gases. For example, ammonia is an indication for kidney disease, methanol for lung cancer, acetone for diabetes, upper respiratory tract for isopropanol. FIG. 7F shows the response of the as-prepared sensors towards ammonia and other common interfering gases, demonstrating the suitability of the proposed samples as highly selective ammonia sensors in biomedical diagnostics applications.

Table I shows a performance comparison between recently reported ammonia sensors. The properties of the ZnO nanorod based sensor are competitive with the other reported ZnO ammonia sensors, demonstrating excellent sensitivity and very fast dynamics. However, unlike the other designs compared, the proposed design involves only a single material, i.e., does not require a heterojunction (e.g. $Cr_2O_3/ZnO$ and $CuO/ZnO$), and does not require doping (e.g. with tungsten or nickel) to augment its high response. In addition, the proposed material can be prepared in a single step, which improves the scalability of fabrication and lessen the demand on complex equipment. Most importantly, by using the rather facile method of changing the solvent environment, a great degree of morphological control has been achieved.

TABLE 1

Performance comparison between reported ZnO ammonia sensors.

| Materials | Structures | Method | Concentration | Response | Response time | Recovery time |
|---|---|---|---|---|---|---|
| $Cr_2O_3/ZnO$ | Thick film | Solid reaction | 300 ppm | 13.7 | 25 s | 75 s |
| $CuO/ZnO$ | Thick film | Solid reaction | 100 ppm | 1.5 | / | / |
| W/ZnO | Thin film | Sol-gel | 100 ppm | 1.5 | 325 | 36 s |
| Ni/ZnO | Thin film | Sol-gel | 100 ppm | 2.52 | 49 s | 58 s |
| ZnO/rGO | Nano-particles | Thermal reduction | 50 ppm | 3.05% | 84 s | 216 s |
| ZnO | Thin film | Sol-gel | 600 ppm | 57.5% | 160 s | 660 s |
| ZnO | Twinned rods | Solvo-thermal | 100 ppm | 25 | 10 s | 36 s |

Gas Sensing Mechanism

The difference in response from the three morphologically distinct samples can be further investigates by examining the sensing mechanism. Typically, a change in the electrical resistance results from a metal oxide gas sensor being exposed to the target gas molecule. For an n-type ZnO semiconductor, the resistance change is mainly due to the adsorption and desorption of oxygen at the sensing material surface. The possible chemical reactions of ammonia with the chemisorbed oxygen molecules can be described as follows:

$$O_2(gas) + 2e^-(ads) \rightarrow 2O^-(ads) \quad \text{(Equation 1)}$$

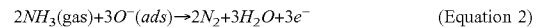
$$2NH_3(gas) + 3O^-(ads) \rightarrow 2N_2 + 3H_2O + 3e^- \quad \text{(Equation 2)}$$

$$e^- + h \cdot \leftrightarrow null \quad \text{(Equation 3)}$$

Figure 8A:
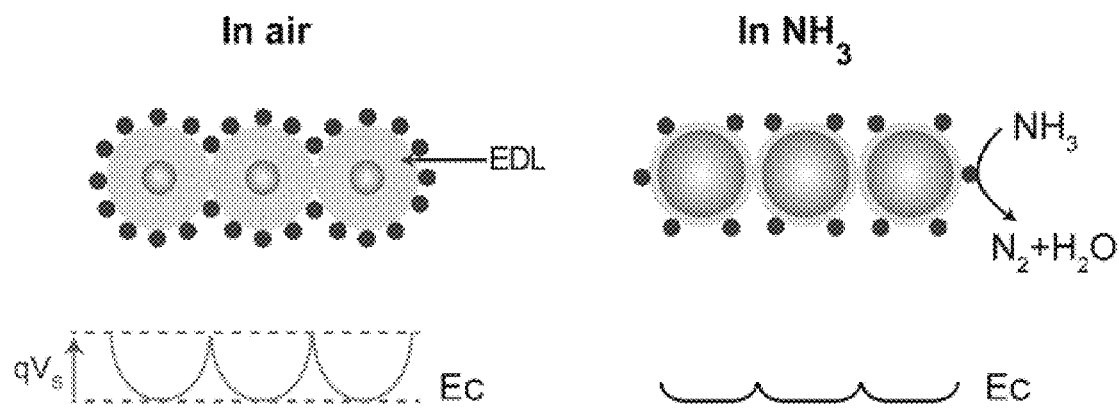
FIG. 8A shows a schematic of the sensing process of ZnO sensors with small grain size, in which $E_c$ denotes the conduction band edge.
Figure 8B:
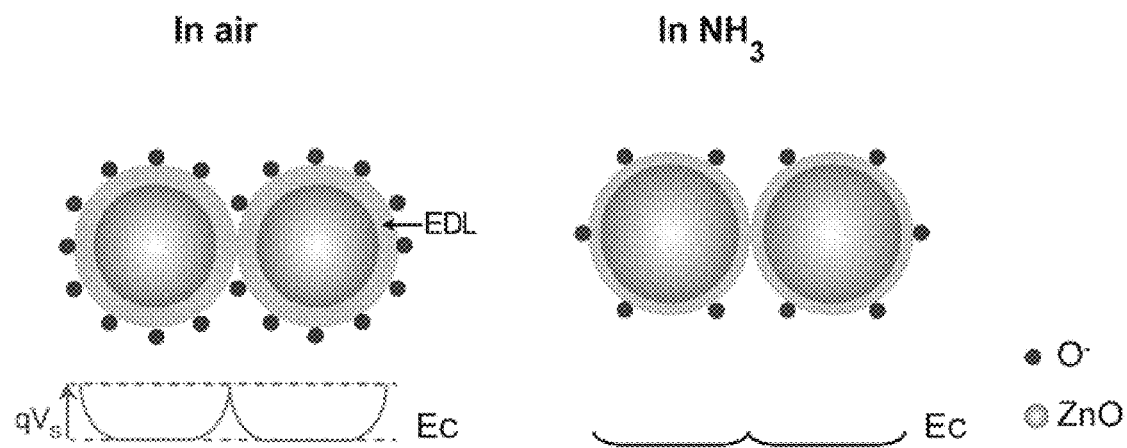
FIG. 8B shows a schematic of the sensing process of ZnO sensors with large grain size.

In air, the atmospheric oxygen absorbed on the surface can be transformed to $O^-$ (ads) by capturing electrons from ZnO. In the temperature range of 100° C. to 500° C., $O^-$ is the dominated adsorbates for a resistance change. As described in Equation 1 and FIGS. 8A and 8B, the reduction of electrons in ZnO causes the formation of an electron depletion layer (EDL) located at the grain boundaries, thus increasing resistance. The conduction band bends upwards and the potential barrier ($qV_s$) is formed, which implies that electrons need to overcome this energy barrier in order to reach the surface.

In the analyte, the adsorbed oxygen species $O^-$ (ads) are consumed by reacting with ammonia, leading to a lower surface coverage of the adsorbates. Electrons are released by the oxygen adsorbates, which reduces the EDL and decreases the resistance. These electrons then return to the conduction band of the ZnO, as described in Equation 2 and Equation 3, resulting in a reduction in the barrier height.

Based on the above analysis, it is evident that the EDL plays an essential role in sensing performance. In general, smaller the crystallite size, the larger the proportion of the EDL layer occupies with respect to the entire crystallite. In fact, it has been reported that the gas induced resistance change is proportional to 1/D, where D is the average grain size. Since the nanorod exhibits the smallest crystal size among the three samples, it has the most depletion, active volume for sensing, thus resulting in the highest response.

Thus, it can be seen that an improved gas sensing layer with ZnO nanostructures/structures and method for fabricating the ZnO nanostructures/structures have been disclosed which eliminates or at least diminishes the disadvantages and problems associated with prior art processes and devices. The present solvent-assisted technique for controlling of the morphology of oxide nanomaterials, which directly maps to various ammonia gas sensing properties. Specifically, by using a polar solvent, the c-axis growth is promoted while growth in the other crystallographic dimensions is suppressed. This results in nanorods with enhancements in gas sensing properties both in terms of sensitivity and dynamic response. Through control of oxide crystal growth, this work paves the way to the rational design of oxide nanomaterials for ammonia and other environmental gas sensing applications.

Although the invention has been described in terms of certain embodiments, other embodiments apparent to those of ordinary skill in the art are also within the scope of this invention. Accordingly, the scope of the invention is intended to be defined only by the claims which follow.

What is claimed is:

1. An ammonia gas sensor comprising:
a gas sensing layer for sensing variation in a concentration of ammonia gas and generating a change in electrical resistance, the gas sensing layer comprising zinc oxide (ZnO) twinned rods and having a thickness of 200 to 400 microns (μm).

2. The ammonia gas sensor of claim 1, wherein the ZnO twinned rods comprise two ZnO rods, which are connected in series.

3. The ammonia gas sensor of claim 1, wherein the ZnO twinned rods have an elongated-hexagonal shape.

4. The ammonia gas sensor of claim 1, wherein the ZnO twinned rods have an aspect ratio of diameter to height being of 1:4 to 1:10, and an average grain size of 32 to 34 nanometers (nm).

5. The ammonia gas sensor of claim 1, wherein the ZnO twinned rods have a diameter of 500 nm to 3 μm, and a height of 5 μm to 10 μm.

6. The ammonia gas sensor of claim 1 further comprising:
a ceramic tube;
two electrodes separately attached to an outer surface of the ceramic tube:
two electrode lines attached to the two electrode respectively; and
a heating element located inside the ceramic tube;
wherein the gas sensing layer electrically connects the two electrodes.

7. The ammonia gas sensor of claim 6, wherein the ceramic tube comprises aluminum oxide; each of the two electrodes is a gold electrode; each of the two electrode line is a platinum wire; the heater is a nickel-chromium coil; and the gas sensing layer at least partially covers the outer surface of the ceramic tube.

8. A gas sensor comprising:
a gas sensing layer for sensing variation in a concentration of a gas and generating a change in electrical resistance, the gas sensing layer comprising a ZnO structure and having a thickness of 200 μm to 400 μm, the ZnO structure being a twin-rod-shaped ZnO structure, a cross-shaped ZnO structure or a flower-shaped ZnO structure.

9. The gas sensor of claim 8 further comprising:
a ceramic tube;
two electrodes separately attached to an outer surface of the ceramic tube;
two electrode lines attached to the two electrode respectively; and
a heating element located inside the ceramic tube;
wherein the gas sensing layer electrically connects the two electrodes.

10. The gas sensor of claim 9, wherein the ceramic tube comprises aluminum oxide; each of the two electrodes is a gold electrode; each of the two electrode line is a platinum wire; the heater is a nickel-chromium coil; and the gas sensing layer at least partially covers the outer surface of the ceramic tube.

11. A method for fabricating a zinc oxide (ZnO) structure comprising:
providing a polar solvent with a predetermined polarity;
mixing zinc nitrate, the polar solvent hexamethylenetramine, polyvinyloyrrolidone and polyvinyl alcohol thereby forming a mixture;
heating the mixture under a pressure thereby forming a precipitate;
separating the precipitate from the heated mixture; and
drying the separated precipitate to form the ZnO structure.

12. The method of claim 11 further comprising calcinating the dried precipitate.

13. The method of claim 11, wherein the ZnO structure is a twin-rod-shaped ZnO structure, a cross-shaped ZnO structure, or a flower-shaped ZnO structure.

14. The method of claim 13, wherein the polar solvent consists of water for forming the twin-rod-shaped ZnO structure; and the polar solvent consists of ethanol for forming the flower-shaped ZnO structure.

15. The method of claim 13, wherein the polar solvent consists of water and ethanol for forming the cross-shaped ZnO structure.

16. The method of claim 15, wherein a volume ratio of the water to the ethanol is of 0.8:1 to 1.2:1.

17. The method of claim 11, wherein the step of providing a polar solvent comprise mixing a plurality of first polar solvents in a volume ratio to form the polar solvent with the predetermined polarity, wherein the plurality of first polar solvents has different polarities.

18. The method of claim 11, wherein the step of providing a polar solvent comprises mixing a first polar solvent and a second polar solvent in a volume ratio to form the polar solvent with the predetermined polarity, wherein the first polar solvent and the second polar solvent have different polarities.

* * * * *